United States Patent
Samain

(10) Patent No.: US 9,622,953 B2
(45) Date of Patent: Apr. 18, 2017

(54) COSMETIC USE OF CATALYTIC OXIDATION COMPOUNDS CHOSEN FROM PORPHYRINS, PHTHALOCYANINES AND/OR PORPHYRAZINES AS DEODORANT AGENT

(71) Applicant: L'Oreal, Paris (FR)

(72) Inventor: Henri Samain, Bievres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/358,950

(22) PCT Filed: Nov. 16, 2012

(86) PCT No.: PCT/EP2012/072893
§ 371 (c)(1),
(2) Date: May 16, 2014

(87) PCT Pub. No.: WO2013/072487
PCT Pub. Date: May 23, 2013

(65) Prior Publication Data
US 2014/0308226 A1    Oct. 16, 2014

Related U.S. Application Data

(60) Provisional application No. 61/564,741, filed on Nov. 29, 2011.

(30) Foreign Application Priority Data

Nov. 18, 2011    (FR) ..................................... 11 60538

(51) Int. Cl.
| | | |
|---|---|---|
| *A61Q 15/00* | (2006.01) | |
| *A61K 8/58* | (2006.01) | |
| *A61K 8/27* | (2006.01) | |
| *A61K 8/49* | (2006.01) | |

(52) U.S. Cl.
CPC .................. *A61K 8/58* (2013.01); *A61K 8/27* (2013.01); *A61K 8/494* (2013.01); *A61Q 15/00* (2013.01); *A61K 2800/58* (2013.01)

(58) Field of Classification Search
CPC .......... A61Q 15/00; A61K 8/27; A61K 8/494; A61K 2800/58
USPC ..................... 8/661, 637.1; 424/65
See application file for complete search history.

(56) References Cited

U.S. PATENT DOCUMENTS 7,429,275 B2 * 9/2008 Hercouet et al. ................. 8/405

FOREIGN PATENT DOCUMENTS

| EP | 0 386 723 A1 | 9/1990 | |
|---|---|---|---|
| EP | 0 834 325 A2 | 4/1998 | |
| FR | 2 954 136 A1 | 6/2011 | |
| JP | 63-246317 A | 10/1988 | |
| JP | 2000-000294 A | 1/2000 | |
| WO | 98/32454 A1 | 7/1998 | |
| WO | 2010/149531 A2 | 12/2010 | |
| WO | WO 2011/050102 A1 * | 4/2011 | ........... A61K 31/555 |

OTHER PUBLICATIONS

STIC Search Report dated Jul. 17, 2014.*
International Search Report and Written Opinion mailed Apr. 29, 2014, issued in corresponding International Application No. PCT/EP2012/072893, filed Nov. 16, 2012, 11 pages.

* cited by examiner

*Primary Examiner* — Eisa Elhilo
(74) *Attorney, Agent, or Firm* — Christensen O'Connor Johnson Kindness PLLC; Juan Zheng; Llewellyn Lawson

(57) ABSTRACT

The present invention relates to the cosmetic use of one or more catalytic oxidation compounds chosen from porphyrins, phthalocyanines and/or porphyrazines as deodorant agent. The present invention also relates to a cosmetic treatment method comprising the application, to a surface of a keratinous substance, of a cosmetic composition comprising, in a cosmetically acceptable medium, one or more catalytic oxidation porphyrin, phthalocyanine and/or porphyrazine compounds.

24 Claims, No Drawings

COSMETIC USE OF CATALYTIC OXIDATION COMPOUNDS CHOSEN FROM PORPHYRINS, PHTHALOCYANINES AND/OR PORPHYRAZINES AS DEODORANT AGENT

The present invention relates to the cosmetic use of one or more catalytic oxidation compounds chosen from porphyrins, phthalocyanines and/or porphyrazines as deodorant agent.

The invention also relates to a method for the cosmetic treatment of human body odours comprising the application, to a surface of a keratinous substance, of a cosmetic composition comprising, in a cosmetically acceptable medium, one or more catalytic oxidation compounds chosen from porphyrins, phthalocyanines and/or porphyrazines.

Unpleasant axillary odours or those originating from other parts of the body, in particular the forehead, the feet or the palm of the hands, are generally generated as a result of the decomposition of sweat, which is odourless when secreted, to give volatile malodorous compounds. This is because the sweat originating from the eccrine or apocrine sweat glands is decomposed via enzymatic reactions by bacteria, which results in the formation of volatile products responsible for unpleasant body odours. For example, it has been found that the presence, on the armpits, of bacteria referred to as aerobic coryneform bacteria is in part the cause of the decomposition of the sweat originating from the apocrine sweat glands and the appearance of unpleasant axillary odours. Thus, different types of deodorant active agents have been developed in the cosmetic field in order to reduce or prevent the formation of unpleasant body odours.

Mention may be made, by way of example, of the substances which inhibit bacteria or those capable of limiting their growth. Use is preferably made, among bactericidal substances, of chlorinated phenol derivatives, such as Triclosan (2,4,4'-trichloro-2'-hydroxydiphenyl ether), hexachlorophene or also chlorhexidine, ethanol and some quaternary ammonium compounds. These substances often exhibit the disadvantage of being toxic. Use may be made, among substances capable of limiting the growth of bacteria, of compounds which chelate transition metals, such as EDTA or DPTA, which make it possible to deprive the environment of the metals necessary for the growth of the bacteria. Such substances exhibit the disadvantage of being ecotoxic.

Mention may also be made of compounds capable of blocking the enzymatic reactions responsible for the formation of the odorous compounds. Mention may be made, by way of illustration, of arylsulfatase, 5-lipoxygenase, aminocylase and β-glucoronidase inhibitors. However, these inhibitors are often specific and remain relatively ineffective with regard to antibacterial substances.

Finally, mention may also be made of substances capable of absorbing unpleasant odours, such as zeolites and cyclodextrins, which are products capable of capturing and retaining within them the molecules responsible for the unpleasant odours. These compounds are difficult to formulate as they can easily interact with other compounds present in the composition, which reduces their effectiveness. Furthermore, the absorption is often selective, which limits the effectiveness of the compositions comprising such compounds.

Furthermore, antiperspirant substances have also been developed in order to reduce the flow of sweat and consequently to minimize the formation of malodorous products. Antiperspirant substances are generally formed from aluminium salts, such as aluminium chloride and aluminium hydroxyhalides, or complexes of aluminium and zirconium. These substances make it possible to reduce the flow of sweat by forming a plug in the sweat duct. Furthermore, aluminium salts are bactericidal and can thus play a direct role with regard to the deodorant effectiveness by reducing the number of bacteria responsible for the decomposition of the sweat.

However, the use of these substances at high concentrations, in particular in a content ranging from 15% to 20% by weight, for the purpose of obtaining good antiperspirant effectiveness, generally exhibits the disadvantage of resulting in formulation difficulties.

Furthermore, compositions based on aluminium salts need to be applied several times to the skin in order to obtain a satisfactory effective antiperspirant effect, which can cause skin irritation in some users.

In an alternative form, a method involving the use of botulinum toxin has been introduced to treat cases of excessive perspiration. However, the need to inject such a toxin at each use greatly limits the exploitation of this method.

In the same way, it is also known to treat excessive perspiration of the feet and hands by ionophoresis, that is to say by using a device capable of applying, to the surfaces to be treated, a direct current which can range from 5 to 25 mA, so as to promote the ionization of a cosmetic product applied beforehand to the skin surface. However, this method also remains tedious to carry out for the user.

There thus exists a real need to make available compounds which do not bring about the abovementioned disadvantages, that is to say which confer a satisfactory deodorant effect while being easy to use on the skin.

The Applicant Company has discovered, surprisingly, that the use, on the surface of a keratinous substance, in particular the skin and/or hair, of one or more catalytic oxidation compounds chosen from porphyrins, phthalocyanines and/or porphyrazines makes it possible to effectively treat unpleasant body odours and to be easy to employ in cosmetic compositions.

This is because it has been found that the cosmetic use of compounds having catalytic oxidation properties chosen from porphyrins, phthalocyanines and/or porphyrazines makes it possible to promote the oxidation of the bacteria responsible for the decomposition of sweat and thus to reduce the formation of the malodorous compounds resulting from this decomposition.

In other words, the compounds in accordance with the present invention exhibit the advantage of preventing the appearance of the unpleasant body odours which result from the decomposition of human sweat by bacteria.

The use, on the skin and/or scalp, of porphyrin, phthalocyanine and/or porphyrazine compounds in accordance with the invention thus makes it possible to result in a satisfactory deodorant effect which can persist for several days.

The porphyrin, phthalocyanine and/or porphyrazine compounds in accordance with the present invention also exhibit the advantage of being able to be used in small amounts within the cosmetic compositions.

A subject-matter of the present invention is thus in particular the cosmetic use of one or more catalytic oxidation compounds chosen from porphyrins, phthalocyanines and/or porphyrazines as deodorant agent.

In other words, the invention relates in particular to the cosmetic use of one or more catalytic oxidation compounds chosen from porphyrins, phthalocyanines and/or porphyrazines for the treatment of body odours.

Likewise, the present invention also relates to a method for the cosmetic treatment of human body odours comprising the application, to a surface of a keratinous substance, in particular the skin and/or hair, of a cosmetic composition comprising, in a cosmetically acceptable medium, one or more catalytic oxidation compounds chosen from porphyrins, phthalocyanines and/or porphyrazines.

The term "keratinous substance" is understood to mean the skin (face, body, lips or scalp), hair, eyelashes, eyebrows, nails or mucous membranes.

Other subject-matters and characteristics, aspects and advantages of the invention will become even more clearly apparent on reading the description and the examples which follow.

The term deodorant agent is understood to mean, within the meaning of the present invention, a compound capable of masking, absorbing, improving, reducing and/or preventing unpleasant body odours resulting from the decomposition of human sweat by bacteria.

The term catalytic oxidation compounds chosen from porphyrins, phthalocyanines and/or porphyrazines is understood to mean, within the meaning of the present invention, porphyrin, phthalocyanine and/or porphyrazine compounds having catalytic oxidation properties.

In particular, the porphyrin, phthalocyanine and/or porphyrazine compounds used in the context of the present invention make it possible to catalyse the oxidation of the bacteria responsible for the decomposition of human sweat to give volatile compounds producing unpleasant body odours.

The porphyrin, phthalocyanine and/or porphyrazine catalytic oxidation compounds used according to the invention differ from the porphyrin, phthalocyanine and/or porphyrazine compounds which do not exhibit catalytic oxidation properties by at least one of the three tests as described below.

The tests mentioned below are described in the case of a porphyrin compound but they can be employed in the same way in the case of a phthalocyanine compound or of a porphyrazine compound.

Test 1: Oxidation of 2,2,6,6-tetramethylpiperidine (TEMP)

In this test, the compound 2,2,6,6-tetramethylpiperidine (TEMP), sold by Sigma Aldrich, acts as a probe which reveals the catalytic activity of a porphyrin compound as oxidation catalyst.

The oxidizing agent used during this test is dissolved oxygen.

A solution comprising a phosphate buffer (pH 7.4), 50 mM of the compound 2,2,6,6-tetramethylpiperidine (TEMP) and a porphyrin compound at 0.5 µM is prepared. The solution is saturated with oxygen. The solution is subjected to daylight.

After 1 hour, electron paramagnetic resonance spectrometry (EPR) is performed on the oxidized form of the compound 2,2,6,6-tetramethylpiperidine (TEMP), which corresponds to the compound (2,2,6,6-tetramethylpiperidin-1-yl)oxyl, known as TEMPO.

In accordance with the scientific publication Lion et al., 1976; Moan and Wold, 1979, the presence of the compound in the TEMPO form reveals the oxidation of the compound 2,2,6,6-tetramethylpiperidine produced by the oxygen and thus the catalytic effect of the porphyrin compound.

$$TEMP + O_2 \rightarrow TEMPO$$

More specifically, this spectrum shows three peaks of equivalent intensity characteristic of the presence of the nitroxide radical in the oxidized form TEMPO.

With a porphyrin compound according to the invention, the appearance of the compound TEMPO is observed after bringing into contact for 1 hour.

Conversely, the presence of a porphyrin which is not within the invention, such as copper chlorophyllin, for example, does not result in the formation of the compound TEMPO.

Test 2: Oxidation of DMPO

In this test, the compound 5,5-dimethyl-1-pyrroline N-oxide (DMPO) acts as a probe which reveals the catalytic activity of a porphyrin compound as oxidation catalyst. The oxidizing agent used during this test is dissolved oxygen.

An aqueous solution, pH=7, comprising 100 mM of DMPO and a porphyrin compound at 100 µM, is prepared. The solution is saturated with oxygen. The solution is subjected to daylight.

After 1 hour, electron paramagnetic resonance spectrometry (EPR) is performed on the oxidized form of the compound 5,5-dimethyl-1-pyrroline N-oxide, known as DMPO-OH. The presence of the form DMPO-OH reveals the oxidation of the compound 5,5-dimethyl-1-pyrroline N-oxide and consequently the catalytic activity of the porphyrin compound.

More specifically, the EPR spectrum is characterized by a hyperfine coupling constant of $a^N = a^H = 14.6$ G.

Test 3: Activation of Hydrogen Peroxide 1 mM of a porphyrin compound is placed in 10-volume hydrogen peroxide, spontaneous pH.

The solution is subjected to daylight.

The content of hydrogen peroxide is then assayed. The porphyrin compound is regarded as within the invention if it reduces the amount of hydrogen peroxide by factor of at least 2 (5 volumes or less).

Thus, the porphyrin, phthalocyanine and/or porphyrazine compounds according to the invention answer to least one of the three tests mentioned above.

Preferably, the invention relates to the cosmetic use of one or more catalytic oxidation porphyrin compounds as deodorant agent.

The catalytic oxidation porphyrin compounds in accordance with the present invention can be cationic, anionic or nonionic.

Preferably, the catalytic oxidation porphyrin compounds in accordance with the present invention are chosen from symmetrical compounds.

The term "symmetrical porphyrin compounds" is understood to mean the porphyrin compounds for which, on the one hand, the radicals located in the meso position are identical to one another and, on the other hand, the radicals located in the β-pyrrole position are identical to one another.

In other words, in accordance with the nomenclature described below, the fact that the radicals located in the meso position are identical to one another means that the radicals located in the α-position are identical. In addition, the fact that the radicals located in the β-pyrrole position are identical to one another means that the radicals located, on the one hand, in the 1, 3, 5 and 7 positions are identical and, on the other hand, that the radicals located in the 2, 4, 6 and 8 positions are identical.

The nomenclature of the porphyrin compound is restated below.

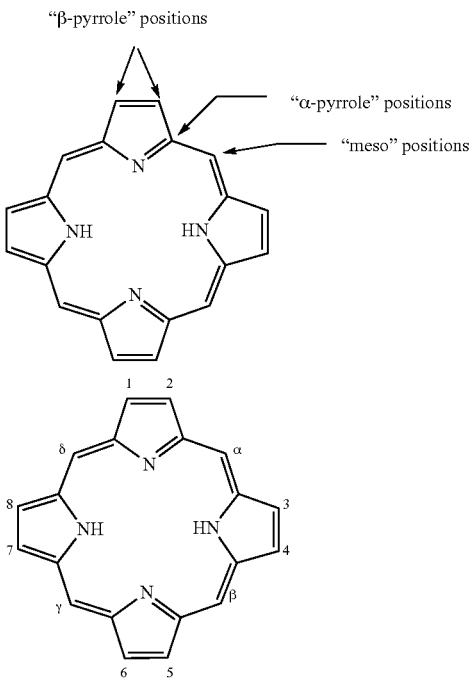

Preferably, the catalytic oxidation porphyrin compounds in accordance with the present invention are chosen from cationic porphyrin compounds, that is to say porphyrin compounds for which the groups placed in the meso or β-pyrrole position are cationic.

The catalytic oxidation porphyrin compound or compounds according to the invention can be chosen from the compounds of following formula (I):

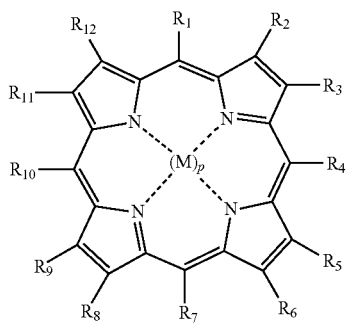

(I)

in which:

$R_2$, $R_3$, $R_5$, $R_6$, $R_8$, $R_9$, $R_{11}$ and $R_{12}$, which are identical or different, represent a hydrogen atom; a linear or branched $C_1$-$C_{30}$ alkyl radical, which can be interrupted by one or more heteroatoms and/or which can be substituted; a linear or branched $C_2$-$C_{30}$ alkenyl radical, which can be interrupted by one or more heteroatoms and/or which can be substituted; or a linear or branched $C_2$-$C_{30}$ alkynyl radical, which can be interrupted by one or more heteroatoms and/or which can be substituted;

$R_2$ and $R_3$, $R_5$ and $R_6$, $R_8$ and $R_9$ and/or $R_{11}$ and $R_{12}$ can respectively form, with the carbon atoms carrying them, an optionally substituted aryl ring, preferably a phenyl ring;

$R_1$, $R_4$, $R_7$ and $R_{10}$, which are identical or different, represent a cationic group, such as an optionally substituted pyridinium group; an anionic group, such as a phenyl radical substituted by a sulfonate $SO_3^-$ group; a linear or branched $C_8$-$C_{30}$ alkyl radical, which can be interrupted by one or more heteroatoms and/or which can be substituted; or a reactive group, which can be chosen from siloxanes, esters and compounds comprising one or more thiol groups; as defined, for example, in the paper Synthesis of "Porphyrin-Linker-Thiol" Molecules with Diverse Linkers for Studies of Molecular-Based Information Storage, by Daniel T. Gryko, Christian Clausen, Kristian M. Roth, Narasaiah Dontha, David F. Bocian, Werner G. Kuhr and Jonathan S. Lindsey, in the paper published in the scientific publication J. Org. Chem., 2000, 65, 7345-7355;

M corresponds to a metal or a metal ion chosen from transition metals and metals from Group IIA (in particular Mg), Group IIB (in particular Zn) and possibly Groups IB to VIIB (in particular Mn) of the Periodic Table of the Elements;

p has the value 0 or 1; in particular, p has the value 1.

In the context of the definitions of the $R_1$, $R_2$, $R_3$, $R_4$, $R_5$, $R_6$, $R_7$, $R_8$, $R_9$, $R_{10}$, $R_{11}$ and $R_{12}$ groups, the term substituted is understood to mean substituted by one or more radicals chosen from i) hydroxyl, ii) $C_1$-$C_4$ alkoxy, iii) acylamino, iv) a halogen atom, preferably chlorine, v) amino, optionally substituted by one or two identical or different $C_1$-$C_{10}$ alkyl radicals, it being possible for the said alkyl radicals to form, with the nitrogen atom which carries them, a 5- to 7-membered heterocycle optionally comprising another heteroatom identical to or different from nitrogen; or vi) a 5- or 6-membered heterocycle which comprises one or more heteroatoms, such as oxygen or nitrogen, which is optionally substituted and which optionally carries at least one cationic charge.

In the context of the definitions of the $R_1$, $R_2$, $R_3$, $R_4$, $R_5$, $R_6$, $R_7$, $R_8$, $R_9$, $R_{10}$, $R_{11}$ and $R_{12}$ groups, the term interrupted is understood to mean interrupted by one or more groups chosen from an oxygen atom; an amino group; an amino group substituted by a linear or branched $C_1$-$C_{10}$ alkyl radical, optionally carrying one or more hydroxyl or linear or branched $C_1$-$C_{10}$ alkoxy groups; an ammonium group substituted by one or two identical or different and linear or branched $C_1$-$C_{10}$ alkyl radicals, optionally carrying one or more hydroxyl or linear or branched $C_1$-$C_{10}$ alkoxy groups; a carbonyl group; or a 5- or 6-membered heterocycle which comprises one or more heteroatoms, such as oxygen or nitrogen, which is optionally substituted and which optionally carries at least one cationic charge.

In the case where p has the value 0, then the porphyrin compounds according to the invention exhibited the following structure (IA):

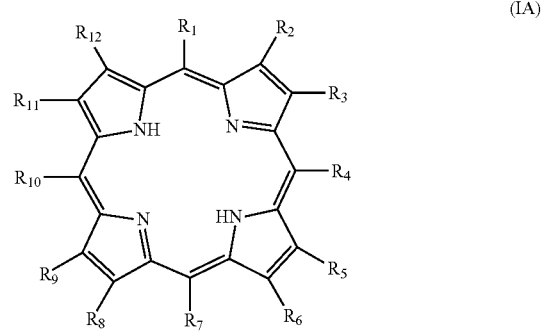

(IA)

in which $R_1$, $R_2$, $R_3$, $R_4$, $R_5$, $R_6$, $R_7$, $R_8$, $R_9$, $R_{10}$, $R_{11}$ and $R_{12}$ have the same meanings as in the formula (I).

In the case where p has the value 1, then the porphyrin compounds according to the invention exhibited the following structure (IB):

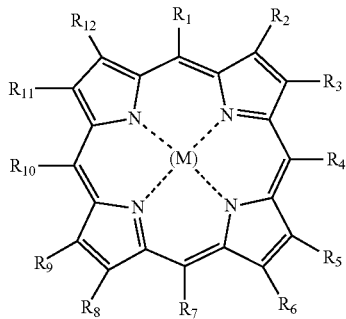

(IB)

in which $R_1$, $R_2$, $R_3$, $R_4$, $R_5$, $R_6$, $R_7$, $R_8$, $R_9$, $R_{10}$, $R_{11}$ and $R_{12}$ have the same meanings as in the formula (I). In this structure, the metal M is connected to the nitrogen atoms forming the pyrrole rings via covalent bonds.

In accordance with one embodiment, the metal M is chosen from transition metals or alkaline earth metals.

The transition metals or alkaline earth metals can be chosen from zinc (Zn), manganese (Mn), iron (Fe), cobalt (Co) and magnesium (Mg).

In accordance with another embodiment, the metal M is a metal belonging to Groups IIA, IIB and VIIB of the Periodic Table of the Elements, such as calcium.

Preferably, the metal M is chosen from transition metals, in particular zinc (Zn) and manganese (Mn), and alkaline earth metals, in particular magnesium (Mg).

More preferably, the metal M is chosen from transition metals and more preferably still zinc (Zn).

In accordance with one embodiment, $R_2$ and $R_3$, $R_5$ and $R_6$, $R_8$ and $R_9$, and $R_{11}$ and $R_{12}$ respectively form, with the carbon atoms carrying them, an optionally substituted aryl ring, preferably a phenyl ring.

In accordance with another embodiment, $R_2$, $R_3$, $R_5$, $R_6$, $R_8$, $R_9$, $R_{11}$ and $R_{12}$ represent a hydrogen atom.

$R_1$, $R_4$, $R_7$ and $R_{10}$, which are identical or different, represent an optionally substituted pyridinium group; a phenyl group substituted by a sulfonate $SO_3^-$ group; or a linear or branched $C_8$-$C_{30}$ alkyl radical, which can be interrupted by one or more heteroatoms and/or which can be substituted.

According to one embodiment, $R_1$, $R_4$, $R_7$ and $R_{10}$ represent an optionally substituted pyridinium group.

According to another embodiment, $R_1$, $R_4$, $R_7$ and $R_{10}$ represent a phenyl group substituted by a sulfonate $SO_3^-$ group.

According to another embodiment, $R_1$, $R_4$, $R_7$ and $R_{10}$ represent a linear or branched $C_8$-$C_{30}$, in particular $C_8$-$C_{18}$, alkyl radical, which can be interrupted by one or more heteroatoms and/or which can be substituted. In particular, $R_1$, $R_4$, $R_7$ and $R_{10}$ represent a $C_8$, $C_{12}$ or $C_{18}$ alkyl radical.

More preferably, $R_1$, $R_4$, $R_7$ and $R_{10}$ represent a pyridinium group, in particular an unsubstituted pyridinium group.

In accordance with a specific embodiment, p=1, M is chosen from transition metals and $R_2$, $R_3$, $R_5$, $R_6$, $R_8$, $R_9$, $R_{11}$ and $R_{12}$ represent a hydrogen atom.

More preferably still, p=1, M is chosen from transition metals, in particular zinc (Zn), $R_2$, $R_3$, $R_5$, $R_6$, $R_8$, $R_9$, $R_{11}$ and $R_{12}$ represent a hydrogen atom and $R_1$, $R_4$, $R_7$ and $R_{10}$ represent an optionally substituted pyridinium group.

In accordance with another embodiment, p=0, $R_2$, $R_3$, $R_5$, $R_6$, $R_8$, $R_9$, $R_{11}$ and $R_{12}$ represent a hydrogen atom and $R_1$, $R_4$, $R_7$ and $R_{10}$ represent an optionally substituted pyridinium group.

In accordance again with an embodiment, p=0, $R_2$, $R_3$, $R_5$, $R_6$, $R_8$, $R_9$, $R_{11}$ and $R_{12}$ represent a hydrogen atom and $R_1$, $R_4$, $R_7$ and $R_{10}$ represent a phenyl group substituted by a sulfonate $SO_3^-$ group.

Preferably, the catalytic oxidation porphyrin compounds employed in the context of the present invention can be chosen from the following compounds:

Cationic porphyrin compound (1)

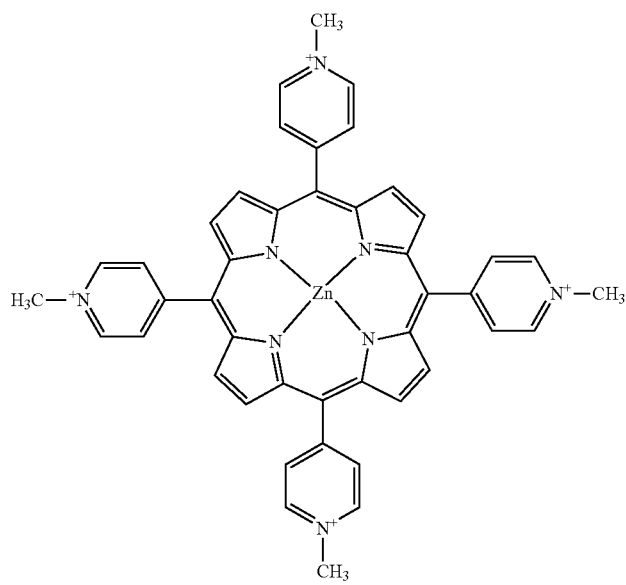

-continued

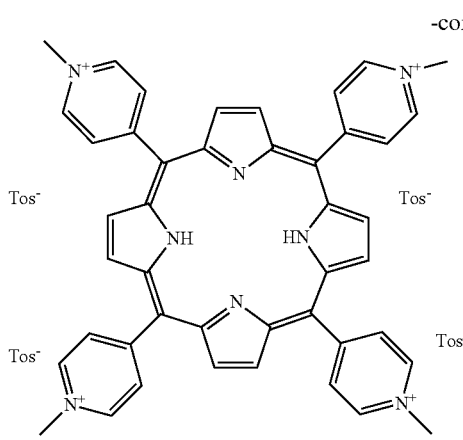 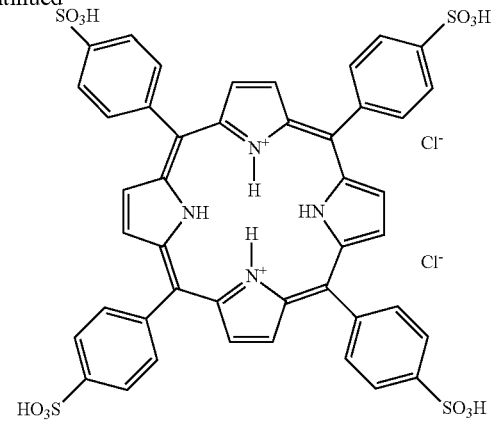

Cationic porphyrin compounds (2) and anionic porphyrin compounds (3)

The present invention also relates to a method for the cosmetic treatment of human body odours comprising the application, to a surface of a keratinous substance, in particular of the skin and/or hair, of a cosmetic composition comprising, in a cosmetically acceptable medium, one or more catalytic oxidation compounds chosen from porphyrins, phthalocyanines and/or porphyrazines.

The catalytic oxidation compound or compounds can be present in the cosmetic composition in a content ranging from $10^{-6}$ to 1% by weight, preferably in a content ranging from $10^{-5}$ to 1% by weight and more particularly in a content ranging from $10^{-4}$ to 0.1% by weight, with respect to the total weight of the cosmetic composition.

Preferably, the cosmetic composition comprises one or more catalytic oxidation porphyrin compounds as defined above.

More preferably still, the cosmetic composition comprises one or more catalytic oxidation porphyrin compounds chosen from the compounds (1), (2), (3) and their mixtures.

The cosmetic composition can comprise two or more different catalytic oxidation porphyrin compounds as defined above.

In particular, the cosmetic composition can comprise two or more different catalytic oxidation porphyrin compounds as defined above chosen from the group consisting of catalytic oxidation cationic porphyrin compounds, catalytic oxidation anionic porphyrin compounds and catalytic oxidation non-ionic porphyrin compounds comprising one or more fatty chains.

The term fatty chain is understood to mean, within the meaning of the present invention, a hydrocarbon chain comprising at least 8 carbon atoms, in particular from 8 to 30 carbon atoms and more particularly from 8 to 18 carbon atoms.

According to a first embodiment, the cosmetic composition can comprise one or more catalytic oxidation cationic porphyrin compounds as defined above and one or more catalytic oxidation anionic porphyrin compounds as defined above.

In particular, the cosmetic composition comprises a catalytic oxidation cationic porphyrin compound of formula (I) and a catalytic oxidation anionic porphyrin compound of formula (I).

In accordance with this first embodiment, the cosmetic composition comprises a catalytic oxidation cationic porphyrin compound of formula (I) in which $R_1$, $R_4$, $R_7$ and $R_{10}$ represent an optionally substituted pyridinium group and a catalytic oxidation anionic porphyrin compound of formula (I) in which $R_1$, $R_4$, $R_7$ and $R_{10}$ represent a phenyl group substituted by a sulfonate $SO_3^-$ group.

Preferably, the cationic and anionic porphyrin compounds of formula (I) employed in the process comprise a metal chosen from transition metals and alkaline earth metals, in particular transition metals According to a second embodiment, the cosmetic composition comprises one or more catalytic oxidation cationic porphyrin compounds as defined above and one or more catalytic oxidation non-ionic porphyrin compounds comprising one or more fatty chains as defined above.

In particular, the cosmetic composition comprises a catalytic oxidation cationic porphyrin compound of formula (I) and a catalytic oxidation non-ionic porphyrin compound comprising one or more fatty chains of formula (I).

In accordance with this embodiment, the cosmetic composition comprises a catalytic oxidation cationic porphyrin compound of formula (I) in which $R_1$, $R_4$, $R_7$ and $R_{10}$ represent an optionally substituted pyridinium group and a catalytic oxidation non-ionic porphyrin compound of formula (I) in which $R_1$, $R_4$, $R_7$ and $R_{10}$ represent a $C_8$-$C_{30}$, in particular $C_8$-$C_{18}$, in particular $C_8$, $C_{12}$ and $C_{18}$ alkyl radical.

Preferably, the catalytic oxidation cationic porphyrin compound and the catalytic oxidation non-ionic porphyrin compound having one or more fatty chains of formula (I) comprise a metal chosen from transition metals.

According to a third embodiment, the cosmetic composition comprises one or more catalytic oxidation anionic porphyrin compounds as defined above and one or more catalytic oxidation non-ionic porphyrin compounds comprising one or more fatty chains as defined above.

In particular, the cosmetic composition comprises a catalytic oxidation anionic porphyrin compound of formula (I) and a catalytic oxidation non-ionic porphyrin compound comprising one or more fatty chains of formula (I).

In accordance with this embodiment, the cosmetic composition can comprise a catalytic oxidation anionic porphyrin compound of formula (I) in which $R_1$, $R_4$, $R_7$ and $R_{10}$ represent a phenyl group substituted by a sulfonate $SO_3^-$ group and a catalytic oxidation non-ionic porphyrin compound of formula (I) in which $R_1$, $R_4$, $R_7$ and $R_{10}$ represent a $C_8$-$C_{30}$, in particular $C_8$-$C_{18}$, in particular $C_8$, $C_{12}$ and $C_{18}$ alkyl radical.

According to one embodiment, the cosmetic composition additionally comprises one or more oxidizing agents.

The presence of one or more oxidizing agents in the cosmetic composition makes it possible to improve the rate of the reaction for the oxidation of the bacteria responsible for the decomposition of human sweat to give malodorous compounds.

Thus, the cosmetic composition can additionally comprise one or more oxidizing agents chosen, for example, from hydrogen peroxide, urea hydrogen peroxide, alkali metal bromates, persalts, such as perborates and persulfates, and enzymes, such as peroxidases and 2- or 4-electron oxidoreductases. In particular, hydrogen peroxide is preferably used.

The cosmetic composition can additionally comprise one or more antiperspirant active agents.

The antiperspirant active agent or agents which can be used according to the invention can be chosen from aluminium and/or zirconium salts, complexes of zirconium hydroxychloride and of aluminium hydroxychloride with an amino acid and/or their mixtures.

Mention may in particular be made, among aluminium salts, of aluminium chlorohydrate in the activated or non-activated form, aluminium chlorohydrex, the aluminium chlorohydrex polyethylene glycol complex, the aluminium chlorohydrex propylene glycol complex, aluminium dichlorohydrate, the aluminium dichlorohydrex polyethylene glycol complex, the aluminium dichlorohydrex propylene glycol complex, aluminium sesquichlorohydrate, the aluminium sesquichlorohydrex polyethylene glycol complex, the aluminium sesquichlorohydrex propylene glycol complex or aluminium sulfate buffered with sodium aluminium lactate.

Mention may in particular be made, among aluminium zirconium salts, of aluminium zirconium octachlorohydrate, aluminium zirconium pentachlorohydrate, aluminium zirconium tetrachlorohydrate or aluminium zirconium trichlorohydrate.

The complexes of zirconium hydroxychloride and of aluminium hydroxychloride with an amino acid are generally known under the name ZAG (when the amino acid is glycine). Mention may be made, among these products, of the aluminium zirconium octachlorohydrex glycine complexes, aluminium zirconium pentachlorohydrex glycine complexes, aluminium zirconium tetrachlorohydrex glycine complexes and aluminium zirconium trichlorohydrex glycine complexes.

Preferably, the antiperspirant active agent is aluminium chlorohydrate in the activated or non-activated form.

The antiperspirant active agent or agents can be present in the cosmetic composition in a content ranging from 0.1% to 50% by weight, preferably in a content ranging from 1% to 30% by weight, with respect to the total weight of the cosmetic composition.

The composition can comprise one or more polymers, in particular those described in the paper entitled "Novel Porphyrin—Incorporated Hydrogels for Photoactive Intraocular Lens Biomaterials", Journal of Physical Chemistry B (2007), 111(3), 527-534.

The term "cosmetically acceptable medium" is understood to mean a medium which is compatible with the skin and/or its superficial body growths, which has a pleasant colour, a pleasant odour and a pleasant feel and which does not cause any unacceptable discomfort (smarting, tightness, redness) liable to dissuade the consumer from using this composition.

The cosmetically acceptable medium generally consists of water or of a mixture of water and of one or more normal organic solvents.

Mention may in particular be made, among suitable solvents, of non-aromatic alcohols, such as ethyl alcohol or isopropyl alcohol, or glycols or glycol ethers, such as, for example, ethylene glycol monomethyl, monoethyl or monobutyl ether, propylene glycol or its ethers, such as, for example, propylene glycol monomethyl ether, butylene glycol, dipropylene glycol, and also diethylene glycol alkyl ethers, such as, for example, diethylene glycol monoethyl ether or monobutyl ether, or alternatively polyols, such as glycerol. Use may also be made, as solvent, of polyethylene glycols and polypropylene glycols, and the mixtures of all these compounds.

The normal solvents described above, if they are present, usually represent from 0.1% to 15% by weight and more preferably from 0.5% to 5% by weight, with respect to the total weight of the composition.

The cosmetic composition can additionally comprise one or more conventional additives well known in the art, such as natural or synthetic thickeners or viscosity regulators; particles; ceramides or pseudoceramides; sequestering agents; solubilizing agents; proteins; reducing agents or antioxidants; vitamins or provitamins; cationic or amphoteric polymers; pH-stabilizing agents; preservatives; acidifying or basifying agents; moisturizing agents; deodorant active agents other than those of the present invention; bactericides; fungicides; lipoamino acids; screening agents; fragrances; colourants or their mixtures.

Preferably, the cosmetic composition does not comprise sequestering agents, in particular sequestering agents capable of capturing the metal of the porphyrin compounds of formula (I).

Preferably, the cosmetic composition comprises one or more sequestering agents in a low content, in particular in a content of less than 1% by weight, more particularly of less than 0.01% by weight, with respect to the total weight of the composition.

The cosmetic composition can comprise one or more particles exhibiting a cationic or anionic surface charge.

In particular, the cosmetic composition can comprise one or more particles having a surface ionic charge opposite that of the porphyrin, phthalocyanine and/or porphyrazine compounds according to the invention.

More particularly, the cosmetic composition can comprise one or more particles having a surface ionic charge opposite that of the porphyrin compounds according to the invention.

Thus, the cosmetic composition can comprise one or more cationic porphyrin compounds as defined above and one or more particles having an anionic surface charge.

In the same way, the cosmetic composition can comprise one or more anionic porphyrin compounds as defined above and one or more particles having a cationic surface charge.

The particles can be inorganic or organic.

Mention may in particular be made, among inorganic particles, of clays, silicates, silica, kaolin, hydroxyapatite or particles formed by alkaline earth metals, transition metals, rare earth metals and alloys of these metals.

In particular, the particles can be of silica and alumina.

Mention may be made, among acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Mention may be made, among basifying agents, by way of example, of aqueous ammonia, alkali metal carbonates, alkanolamines, such as mono-, di- and triethanolamines and their derivatives, sodium hydroxide, potassium hydroxide and the compounds of following formula (VI):

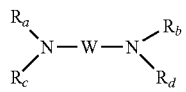

(VI)

in which W is a propylene residue optionally substituted by a hydroxyl group or a $C_1$-$C_4$ alkyl radical and $R_a$, $R_b$, $R_c$ and $R_d$, which are identical or different, represent a hydrogen atom or a $C_1$-$C_4$ alkyl or $C_1$-$C_4$ hydroxyalkyl radical.

Preferably, the cosmetic composition comprises one or more basifying agents chosen from alkanolamines, in particular triethanolamine, and sodium hydroxide.

The pH of the composition in accordance with the invention is generally between 3 and 12 approximately, preferably between 5 and 11 approximately and more particularly still from 6 to 8.5.

The deodorant compositions according to the invention intended for the cosmetic use can be provided in the form of lotions, creams or fluid gels dispensed as an aerosol spray, as a pump-action spray or as a roll-on, in the form of thick creams dispensed in tubes or in stick-form grid, or in the form of sticks, and can comprise, in this regard, the ingredients generally used in products of this type and which are well-known to a person skilled in the art, provided that they do not interfere with the porphyrin compounds described the present invention.

The cosmetic compositions according to the invention can also be provided in the form of shampoos.

The deodorant compositions according to the invention intended for the cosmetic use can comprise at least one aqueous phase. They are in particular formulated as aqueous lotions or as a water-in-oil emulsion, oil-in-water emulsion or multiple emulsion (oil-in-water-in-oil or water-in-oil-in-water triple emulsion) (such emulsions are known and described, for example by C. Fox in Cosmetics and Toiletries, November 1986—Vol. 101—pages 101-112).

The cosmetic compositions according to the invention can be provided in the form of an oil-in-water or water-in-oil emulsion.

The emulsification processes which can be used are of the paddle or propeller, rotor-stator and HPH type.

It is also possible, by HPH (between 50 and 800 bar), to obtain stable dispersions with drop sizes which can be as small as 100 nm.

The emulsions generally comprise one or more emulsifying surfactants chosen from amphoteric, anionic, cationic or non-ionic emulsifying surfactants, used alone or as a mixture.

The emulsifiers are appropriately chosen according to the emulsion to be obtained (W/O or O/W).

Mention may be made, as emulsifying surfactants which can be used for the preparation of the W/O emulsions, for example, of alkyl esters or ethers of sorbitan, of glycerol or of sugars; or silicone surfactants, such as dimethicone copolyols, for example the mixture of cyclomethicone and of dimethicone copolyol sold under the name DC 5225 C by Dow Corning, and alkyl dimethicone copolyols, such as lauryl methicone copolyol, sold under the name Dow Corning 5200 Formulation Aid by Dow Corning, cetyl dimethicone copolyol, such as the product sold under the name Abil EM 90R by Goldschmidt, and the mixture of cetyl dimethicone copolyol, of polyglyceryl (4 mol) isostearate and of hexyl laurate sold under the name Abil WE O9 by Goldschmidt. It is also possible to add thereto one or more coemulsifiers which, advantageously, can be chosen from the group consisting of polyol alkyl esters.

Mention may in particular be made, as polyol alkyl esters, of polyethylene glycol esters, such as PEG-30 Dipolyhydroxystearate, such as the product sold under the name Arlacel P135 by ICI.

Mention may be made, as glycerol and/or sorbitan esters, for example, of polyglyceryl isostearate, such as the product sold under the name Isolan GI 34 by Goldschmidt; sorbitan isostearate, such as the product sold under the name Arlacel 987 by ICI; sorbitan glyceryl isostearate, such as the product sold under the name Arlacel 986 by ICI, and their mixtures.

Mention may be made, for the O/W emulsions, for example, as emulsifying surfactants, of non-ionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG-100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by Henkel under the respective names Plantaren 2000 and Plantaren 1200, cetearyl glucoside, optionally as a mixture with cetearyl alcohol, sold, for example, under the name Montanov 68 by Seppic, under the name Tegocare CG90 by Goldschmidt and under the name Emulgade KE3302 by Henkel, and arachidyl glucoside, for example in the form of the mixture of arachidyl and behenyl alcohols and of arachidyl glucoside sold under the name Montanov 202 by Seppic. According to a specific embodiment of the invention, the mixture of the alkyl polyglucoside as defined above with the corresponding fatty alcohol can be in the form of a self-emulsifying composition, for example as described in the document WO-A-92/06778.

When an emulsion is involved, the aqueous phase of the latter can comprise a non-ionic vesicular dispersion prepared according to known processes (Bangham, Standish and Watkins, J. Mol. Biol., 13, 238 (1965), FR 2 315 991 and FR 2 416 008).

Preferably, the cosmetic composition comprises one or more emulsifying surfactants, in particular non-ionic emulsifiers, such as oxyalkylenated esters of fatty acids, for example the PEG-100 stearate/glyceryl stearate mixture, and ethers of fatty alcohol and of sugar, such as cetearyl glucoside, optionally as a mixture with cetearyl alcohol.

According to one embodiment, the cosmetic composition can be aqueous.

The term "aqueous" is understood to mean, within the meaning of the invention, a composition having a content of free water of greater than 60% by weight, preferably of greater than 70% by weight, with respect to the total weight of the composition.

According to another embodiment, the cosmetic composition can be anhydrous.

In particular, the cosmetic composition can be anhydrous in the case where the porphyrin compounds comprise, in their structure, one or more fatty chains.

The term "anhydrous" is understood to mean, within the meaning of the invention, a composition having a content of free or added water of less than 3% by weight and preferably having a content of added water of less than 1% by weight, with respect to the total weight of the composition.

Preferably, the anhydrous cosmetic composition does not comprise water.

In accordance with this embodiment, the cosmetic composition can be an anhydrous film.

Within the meaning of the present invention, the term "film" is understood to mean a thin solid which can be grasped. The term "thin" is understood to mean a solid having a thickness of at most 1000 µm. This film generally has an appropriate size in order to be able to be easily handled by the user. It can have a square, rectangular or disc shape, or any other shape. Each film generally has a thickness of 10 lam to 1000 µm, preferably of 20 to 500 µm and better still of 50 to 300 µm. It can have a surface area of 10 à 800 cm² and preferably of 100 à 600 cm².

In particular, the anhydrous cosmetic film can be impregnated at its surface with the porphyrin compound or compounds according to the invention.

The cosmetic composition is applied to a surface of a keratinous substance, in particular the armpits, the skin and/or the hair, in particular on the armpits.

The cosmetic composition may or may not be rinsed off after having been applied to the surface of the keratinous substance. Preferably, the cosmetic composition is not rinsed off.

Prior to the application, to the surface of a keratinous substance, of a cosmetic composition comprising the catalytic oxidation compound or compounds, it is possible to apply, to the said surface, a cosmetic composition which makes it possible to prepare the surface of the keratinous substance to be treated.

The term "preparation composition" is understood to mean a composition applied beforehand which makes it possible to improve the retention of the porphyrin, phthalocyanine and/or porphyrazine compound, in particular towards rinsing and washing.

In particular, the preparation composition makes it possible to improve the retention of the porphyrin compound, in particular towards rinsing and washing.

Thus, in the case of the application of a cationic porphyrin compound, it is possible to apply an anionic compound to the skin, for example an anionic compound comprising one or more carboxylic or sulfonic functional groups, such as an anionic resin, and in particular an anionic copolymer, such as that sold under the name Ultrahold Strong by BASF, or a sulfonic copolymer, such as that sold under the name AQ 1350 by National Starch.

It is also possible to modify the surface of the skin in order to create anionic sites, in particular thiol sites.

Thus, the preparation composition can comprise one or more thiol compounds (thioglycolic acid, cysteamine, cysteine, and the like) or a sulfite.

It is also possible to apply, to the skin, anionic salts intended to render the porphyrin compound insoluble, such as a carbonate, hydrogencarbonate or phosphate ion.

In the case of the application of an anionic porphyrin compound, it is possible to apply, to the skin, a cationic compound comprising amine groups or quaternary ammonium functional groups, such as the compound sold under the Lupamine name by BASF or polymers known as ionenes.

It is also possible to apply, to the skin, cationic salts intended to render the porphyrin compound insoluble, such as a divalent (calcium) ion.

Preferably, the stage of preparation of the surface of the keratinous substance consists in applying, to the said surface, a cosmetic composition comprising, in a cosmetically acceptable medium, one or more reducing compounds.

Advantageously, after the application of the cosmetic composition comprising the porphyrin, phthalocyanine and/or porphyrazine compound or compounds according to the invention, it is possible to apply a cosmetic composition in order to retain the wear property of the said porphyrin compounds on the surface of the keratinous substance.

Preferably, a cosmetic composition comprising, in a cosmetically acceptable medium, one or more polymers is applied to the said surface.

The application of the cosmetic composition comprising the polymer or polymers makes it possible to efficiently retain the porphyrin, phthalocyanine and/or porphyrazine compounds at the surface of the keratinous substance.

It is also possible to place, on the skin, a composition which induces an occlusive effect, such as a resin, a wax or an adhesive patch.

In an alternative form, after the application of the cosmetic composition comprising the porphyrin, phthalocyanine and/or porphyrazine compound or compounds according to the invention, it is possible to apply a film to the surface of the treated keratinous substance and in particular an oxygen-permeable film, in order to facilitate the oxidation of the bacteria.

Furthermore, after the application of the cosmetic composition comprising the porphyrin, phthalocyanine and/or porphyrazine compound or compounds according to the invention, it is possible to apply, to the surface of the treated keratinous substance, a composition comprising one or more active agents chosen from bactericides, fungicides and/or powders.

The oxidizing agent or agents can be employed in the cosmetic composition in accordance with the present invention or in a separate cosmetic composition.

The cosmetic composition comprising the oxidizing agent or agents can thus be applied before or after the cosmetic composition comprising the catalytic oxidation porphyrin, phthalocyanine and/or porphyrazine compounds according to the invention.

Alternatively, is also possible to apply a cosmetic composition comprising, in a cosmetically acceptable medium, one or more compounds capable of releasing one or more oxidizing agents.

By way of example, the said cosmetic composition can comprise a mixture comprising glucose oxidase and glucose.

According to one embodiment, the method for the cosmetic treatment of body odours can comprise the following stages:
 a cosmetic composition comprising, in a cosmetically acceptable medium, one or more catalytic oxidation cationic porphyrin compounds as defined above is applied to a surface of a keratinous substance,
 a cosmetic composition comprising, in a cosmetically acceptable medium, one or more catalytic oxidation anionic porphyrin compounds as defined above is applied to the said surface.

In accordance with this embodiment, the cosmetic composition comprising the catalytic oxidation anionic porphyrin compound can be applied, immediately or not immediately, after the cosmetic composition comprising the catalytic oxidation cationic porphyrin compound (or vice versa).

According to one embodiment, the method for the cosmetic treatment of body odours can comprise the following stages:
 a cosmetic composition comprising, in a cosmetically acceptable medium, one or more catalytic oxidation cationic porphyrin compounds as defined above is applied to a surface of a keratinous substance,
 a cosmetic composition comprising, in a cosmetically acceptable medium, one or more catalytic oxidation non-ionic porphyrin compounds comprising one or more fatty chains as defined above is applied to the said surface.

In accordance with this embodiment, the cosmetic composition comprising the catalytic oxidation non-ionic porphyrin compound having one or more fatty chains can be applied, immediately or not immediately, after the cosmetic composition comprising the catalytic oxidation cationic porphyrin compound (or vice versa).

According to one embodiment, the method for the cosmetic treatment of body odours can comprise the following stages:
- a cosmetic composition comprising, in a cosmetically acceptable medium, one or more catalytic oxidation anionic porphyrin compounds as defined above is applied to a surface of a keratinous substance,
- a cosmetic composition comprising, in a cosmetically acceptable medium, one or more catalytic oxidation non-ionic porphyrin compounds comprising one or more fatty chains as defined above is applied to the said surface.

In accordance with this embodiment, the cosmetic composition comprising the catalytic oxidation non-ionic porphyrin compound having one or more fatty chains can be applied, immediately or not immediately, after the cosmetic composition comprising the catalytic oxidation anionic porphyrin compound (or vice versa).

The present invention also relates to the use of a cosmetic composition comprising, in a cosmetically acceptable medium, one or more porphyrin, phthalocyanine and/or porphyrazine compounds as described above for the treatment of human body odours.

In particular, the present invention relates to the use of a cosmetic composition comprising, in a cosmetically acceptable medium, one or more catalytic oxidation porphyrin compounds as described above for the treatment of human body odours.

The following examples serve to illustrate the present invention without, however, exhibiting a limiting nature.

EXAMPLE 1

Use is made of a porphyrin compound having the following structure:

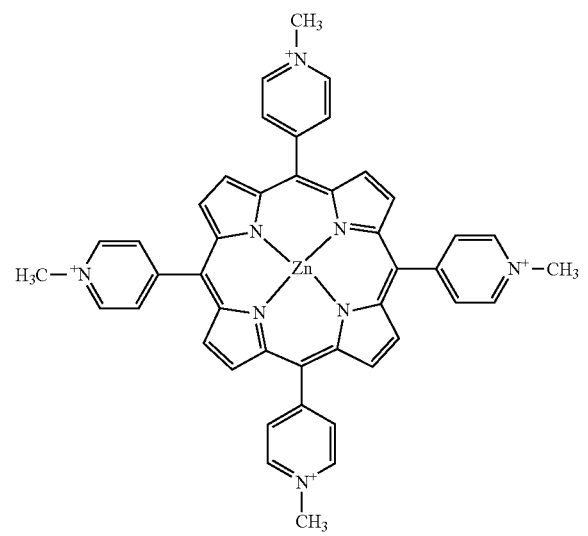

This porphyrin compound responds positively in particular to Tests 1 and 2 as described above.

The following protocol is carried out:
1) Human sweat is collected. During this collecting, the sweat is frozen.
2) The sweat is subsequently placed in a flask, so that there is an air phase above, once the flask is closed. 1 gram of sweat is placed in a 20 ml flask.
3) The porphyrin compound is placed in the flask in a proportion of 0.1 mg.
4) The flask is closed and incubated at 37° C. A test is then carried out which consists in sniffing the flask at t=4 hours and at t=16 hours.

The test is carried out blind and in comparison with a flask of sweat not comprising additive, a flask of sweat comprising a porphyrin compound not included in the present invention, such as cupric chlorophyllin, and a flask of sweat comprising 0.1 mg of triclosan.

The test is carried out by a panel composed of 8 testers who record their impression in terms of odorous intensity and of quality (ranging from neutral up to repulsive) and the mean of the impressions is produced.

It is found that the best impressions are reaped by the flask comprising the porphyrin compound according to the invention.

EXAMPLE 2

The same trial is carried out as in Example 1, except that the active agents are the metal-free cationic porphyrin compound. An anionic porphyrin is also included in the test:

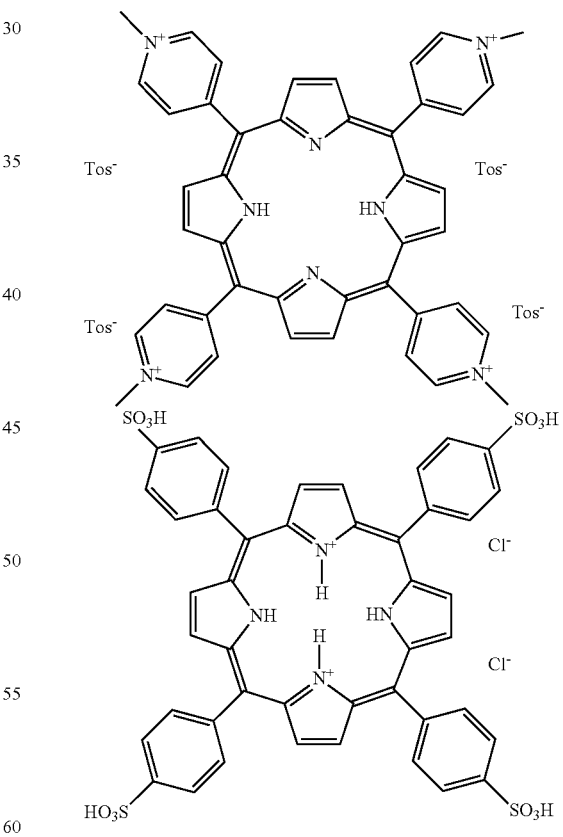

The cationic porphyrin compound responds positively to Tests 1 and 2 as described above and the anionic porphyrin compound responds positively to Tests 1 and 3.

1 mg of each of the porphyrin compounds is introduced into flasks comprising sweat collected in the same way as in Example 1.

It is found that the cationic and anionic porphyrin compounds according to the invention are effective.

EXAMPLE 3

Each of the porphyrin compounds used in Examples 1 and 2 is introduced into water, in a proportion of a concentration of 0.1%.

The cosmetic composition is applied to the skin, at the armpits, and it is found that a satisfactory deodorant effect is obtained for 8 hours.

The invention claimed is:

1. Method for the treatment of body odors, comprising applying on the skin one or more catalytic oxidation compounds chosen from porphyrins, phthalocyanines and/or porphyrazines as deodorant agent, the porphyrins compounds being chosen from the compounds of following formula (I):

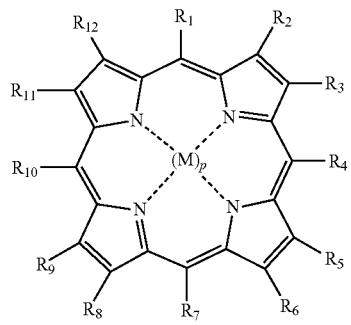

(I)

in which:
$R_2$, $R_3$, $R_5$, $R_6$, $R_8$, $R_9$, $R_{11}$, and $R_{12}$, which are identical or different, represent a hydrogen atom; a linear or branched $C_1$-$C_{30}$ alkyl radical, optionally interrupted by one or more heteroatoms and/or optionally substituted; a linear or branched $C_2$-$C_{30}$ alkenyl radical, optionally interrupted by one or more heteroatoms and/or optionally substituted; or a linear or branched $C_2$-$C_{30}$ alkynyl radical, optionally interrupted by one or more heteroatoms and/or optionally substituted; or
$R_2$ and $R_3$, $R_5$ and $R_6$, $R_8$ and $R_9$, and/or $R_{11}$ and $R_{12}$ respectively form, with the carbon atoms carrying them, an optionally substituted aryl ring;
$R_1$, $R_4$, $R_7$, and $R_{10}$, which are identical or different, represent a cationic group; an anionic group; a linear or branched $C_8$-$C_{30}$ alkyl radical, optionally interrupted by one or more heteroatoms and/or optionally substituted; or a reactive group, chosen from siloxanes, esters and compounds comprising one or more thiol groups;
M corresponds to a metal or a metal ion chosen from transition metals and metals from Group IIA, Group IIB and Groups IB to VIIB of the Periodic Table of the Elements; and
p has the value 0 or 1.

2. Method according to claim 1, characterized in that the compound or compounds are chosen from catalytic oxidation porphyrin compounds.

3. Method according to claim 2, characterized in that the metal M is a transition metal or alkaline earth metal chosen from zinc (Zn), manganese (Mn), iron (Fe), cobalt (Co), and magnesium (Mg).

4. Method according to claim 2, characterized in that the metal M is a metal belonging to Groups IIA, IIB and VIIB of the Periodic Table of the Elements.

5. Method according to claim 2, characterized in that $R_2$ and $R_3$, $R_5$ and $R_6$, $R_8$ and $R_9$, and $R_{11}$ and $R_{12}$ respectively form, with the carbon atoms carrying them, an optionally substituted aryl ring.

6. Method according to claim 2, characterized in that $R_2$, $R_3$, $R_5$, $R_6$, $R_8$, $R_9$, $R_{11}$ and $R_{12}$ represent a hydrogen atom.

7. Method according to claim 2, characterized in that $R_1$, $R_4$, $R_7$ and $R_{10}$ represent an optionally substituted pyridinium group.

8. Method according to claim 2, characterized in that $R_1$, $R_4$, $R_7$ and $R_{10}$ represent a phenyl group substituted by a sulfonate $SO_3^-$ group.

9. Method according to claim 2, characterized in that $R_1$, $R_4$, $R_7$ and $R_{10}$ represent a linear or branched $C_8$-$C_{30}$ alkyl radical, optionally interrupted by one or more heteroatoms and/or optionally substituted.

10. Method according to claim 2, characterized in that the catalytic oxidation porphyrin compounds are chosen from the following compounds:

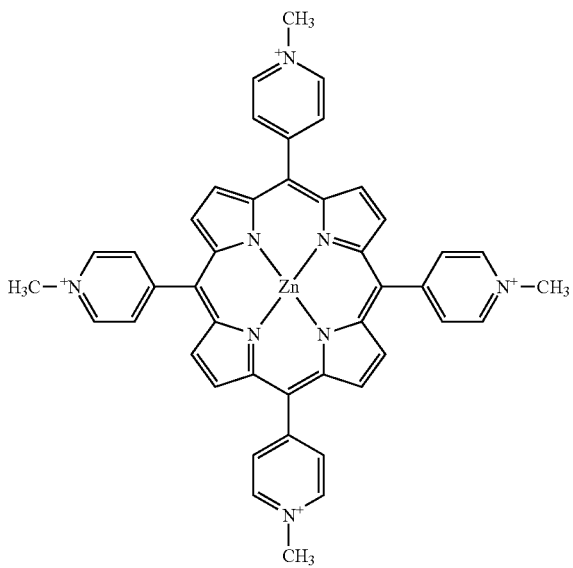

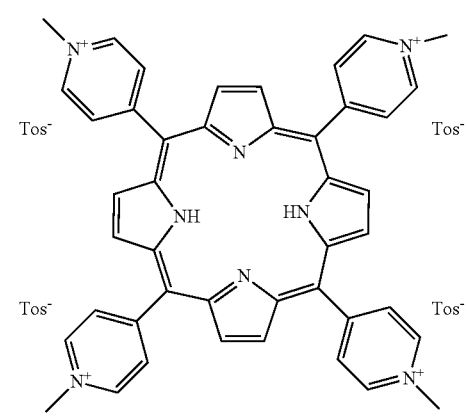

-continued

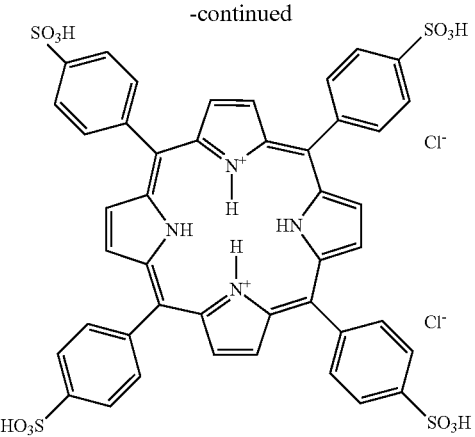

11. Cosmetic treatment of human body odours method comprising the application, to a surface of the skin, of a cosmetic composition comprising, in a cosmetically acceptable medium, one or more catalytic oxidation compounds chosen from porphyrins, phthalocyanines and/or porphyrazines as defined according to claim 1, wherein the porphyrins compounds are chosen from the compounds of following formula (I):

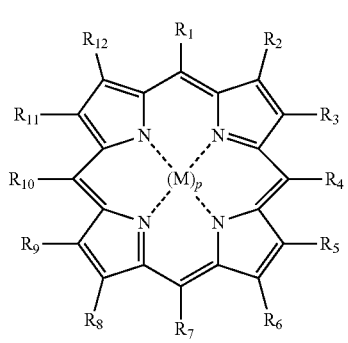

in which:
$R_2$, $R_3$, $R_5$, $R_6$, $R_8$, $R_9$, $R_{11}$, and $R_{12}$, which are identical or different, represent a hydrogen atom; a linear or branched $C_1$-$C_{30}$ alkyl radical, optionally interrupted by one or more heteroatoms and/or optionally substituted; a linear or branched $C_2$-$C_{30}$ alkenyl radical, optionally interrupted by one or more heteroatoms and/or optionally substituted; or a linear or branched $C_2$-$C_{30}$ alkynyl radical, optionally interrupted by one or more heteroatoms and/or optionally substituted;
$R_2$ and $R_3$, $R_5$ and $R_6$, $R_8$ and $R_9$, and/or $R_{11}$ and $R_{12}$ can respectively form, with the carbon atoms carrying them, an optionally substituted aryl ring;
$R_1$, $R_4$, $R_7$, and $R_{10}$, which are identical or different, represent a cationic group; an anionic group; a linear or branched $C_8$-$C_{30}$ alkyl radical, optionally interrupted by one or more heteroatoms and/or optionally substituted; or a reactive group, optionally chosen from siloxanes, esters and compounds comprising one or more thiol groups;
M corresponds to a metal or a metal ion chosen from transition metals and metals from Group IIA, Group IIB and Groups IB to VIIB of the Periodic Table of the Elements; and
p has the value 0 or 1.

12. Cosmetic treatment method according to claim 11, characterized in that the cosmetic composition comprises two or more different catalytic oxidation porphyrin compounds chosen from catalytic oxidation cationic porphyrin compounds, catalytic oxidation anionic porphyrin compounds and/or catalytic oxidation non-ionic porphyrin compounds comprising one or more fatty chains.

13. Cosmetic treatment method according to claim 11, characterized in that the cosmetic composition additionally comprises one or more oxidizing agents.

14. Method according to claim 1, characterized in that $R_2$ and $R_3$, $R_5$ and $R_6$, $R_8$ and $R_9$, and/or $R_{11}$ and $R_{12}$ respectively form, with the carbon atoms carrying them, a phenyl ring.

15. Method according to claim 1, characterized in that $R_1$, $R_4$, $R_7$, and $R_{10}$, which are identical or different, represent optionally substituted pyridinium; or phenyl substituted by a sulfonate $SO_3^-$ group.

16. Method according to claim 1, characterized in that M corresponds to a metal or a metal ion chosen from Mg, Zn, and Mn.

17. Method according to claim 1, characterized in that p has the value 1.

18. Method according to claim 2, characterized in that the metal M is calcium.

19. Method according to claim 2, characterized in that $R_2$ and $R_3$, $R_5$ and $R_6$, $R_8$ and $R_9$, and $R_{11}$ and $R_{12}$ respectively form, with the carbon atoms carrying them, a phenyl ring.

20. Method according to claim 2, characterized in that $R_1$, $R_4$, $R_7$ and $R_{10}$ represent a linear or branched $C_8$-$C_{18}$ alkyl radical, optionally interrupted by one or more heteroatoms and/or optionally substituted.

21. Cosmetic treatment method according to claim 11, characterized in that $R_2$ and $R_3$, $R_5$ and $R_6$, $R_8$ and $R_9$, and/or $R_{11}$ and $R_{12}$ respectively form, with the carbon atoms carrying them, a phenyl ring.

22. Cosmetic treatment method according to claim 11, characterized in that $R_1$, $R_4$, $R_7$, and $R_{10}$, which are identical or different, represent optionally substituted pyridinium; or phenyl substituted by a sulfonate $SO_3^-$ group.

23. Cosmetic treatment method according to claim 11, characterized in that M corresponds to a metal or a metal ion chosen from Mg, Zn, and Mn.

24. Cosmetic treatment method according to claim 11, characterized in that p has the value 1.

* * * * *